(12) United States Patent
Atzinger et al.

(10) Patent No.: US 7,114,849 B2
(45) Date of Patent: Oct. 3, 2006

(54) MEDICAL IMAGING DEVICE

(75) Inventors: Franz Atzinger, Nürnberg (DE); Peter Scheuering, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/081,459

(22) Filed: Mar. 16, 2005

(65) Prior Publication Data
US 2005/0232397 A1    Oct. 20, 2005

(30) Foreign Application Priority Data
Mar. 30, 2004  (DE) ............... 10 2004 015 540

(51) Int. Cl.
*A61B 6/04*    (2006.01)
(52) U.S. Cl. .................................. 378/206; 378/62
(58) Field of Classification Search ............. 378/62, 378/98, 98.8, 98.11, 98.12, 116, 205, 206; 250/370.08, 370.09
See application file for complete search history.

(56) References Cited

U.S. PATENT DOCUMENTS

| 5,123,056 A | 6/1992 | Wilson | 382/132 |
|---|---|---|---|
| 6,097,833 A | 8/2000 | Lobregt et al. | 382/130 |
| 6,731,783 B1 * | 5/2004 | Tsujii | 382/132 |
| 6,895,076 B1 * | 5/2005 | Halsmer et al. | 378/98.12 |
| 6,944,265 B1 * | 9/2005 | Warp et al. | 378/98.12 |

FOREIGN PATENT DOCUMENTS

| DE | 41 02 729 C2 | 6/1991 |
|---|---|---|
| DE | 694 25 416 T2 | 5/1995 |
| DE | 197 35 112 A1 | 2/1999 |
| DE | 102 44 609 A1 | 4/2004 |

* cited by examiner

*Primary Examiner*—Courtney Thomas

(57) ABSTRACT

Radiographic imaging device with a radiographic source and a digital radiographic detector, which are movable in their positioning in relation to a patient, and with a control device for movement control and for creating a radiographic image which can be output, with an optical marking device (14) provided at the radiographic source (2) which can be used to mark the height ($h_1$–$h_2$) of the area to be recorded on the patient (P) and the control device (10) being embodied to automatically determine the required height and number of radiographic images to be recorded, where necessary to be joined together for output of an overall image depicting the entire patient area and the recording positions of the radiographic source (2) and of the radiographic detector (3) in relation to the defined height of the patient area.

12 Claims, 2 Drawing Sheets

MEDICAL IMAGING DEVICE

CROSS REFERENCE TO RELATED APPLICATIONS

This application claims priority to the German application No. 10 2004 015 540.2, filed Mar. 30, 2004 which is incorporated by reference herein in its entirety.

FIELD OF INVENTION

The invention relates to a radiographic imaging device with a radiographic source and a radiographic detector which can be moved for positioning in relation to a patient, and with a control device to control their movement and to generate a radiographic image which can be output.

BACKGROUND OF INVENTION

In modern x-ray-based diagnostics there is an ever increasing need to examine large areas, such the complete spinal column or the leg area to diagnose the settings of bones for example. In such cases the patient is scanned in a standing position (or for patients unable to stand, lying down) with the radiographic imaging device, that is a normal x-ray device comprising an x-ray tube and an x-ray detector. As a rule the detector features a film cassette measuring 40×120 cm, provided this is of sufficient size to capture an image of the entire area under examination. Alternatively it is known that smaller film cassettes can be used with a number storage foil images which record images of the area under examination and these can then be glued together to produce an overall image. This procedure is cumbersome and complicated and in addition the storage foil needs to be developed which requires a relatively long time, so that diagnosis cannot be undertaken contemporaneously.

From the subsequently published German Patent Application DE 102 44 609.1 the use of a digital radiography detector, that is of a known flat semiconductor detector for recording images, and moving this together with the radiation source in relation to the patient and recording radiographic images in different positions, which are subsequently joined together by the control device to form an overall image is known.

SUMMARY OF INVENTION

An object addressed by the invention is that of specifying a radiographic imaging device designed for simple operation, which very easily makes it possible for the user to define the area under examination to be recorded, especially when this is larger than the height of the active surface of the digital radiographic detector.

To resolve this problem, with a radiographic imaging device of the type mentioned at the start, in accordance with the invention, there is provision for an optical light marking device provided in the radiographic source to be able to mark on the patient the height of the area of the patient to be recorded and for the control device to be embodied to automatically determine the required number and height of the radiographic images to be recorded and if necessary to be joined together in order to output an overall image depicting the entire height of the area of the patient, and the recording positions of the radiographic source and of the radiographic detector depending on the defined height of the area of the patient.

The radiographic imaging in accordance with the invention offers a very simple option for setting up the device to record images and for defining the area of the patient to be recorded. Use is made of an optical light marking device, e.g. in the form of a light or laser sight which is expediently integrated into the diaphragm of the radiographic source, in order to project an optical light marking onto the digital radiographic detector, i.e. to illuminate it, in order to define the height of the area under examination. On the basis of the height defined in this way or the setting parameters of the marking device, the control device, which knows the geometrical circumstances, especially the distance between the radiographic source or position of the marking device and the radiographic detector, is in a position to precisely determine the imaging area produced on the plane of the radiation detector, in order to establish from this knowledge the number of images which need to be recorded to produce an image of the entire area under examination, as well as the height of the individual images which in their entirety then correspond to the height of the examination area. In addition the relevant recording positions into which the radiographic source and detector are moved synchronously via the control device, expediently under automatic control, is established.

If all parameters are known, automatic illumination mode can be allowed directly, in the framework of which the control unit advantageously moves the radiographic source and the radiographic detector synchronously into the relevant recording positions, controls the image recording there and executes the sequence through to the end in order to finally output the overall image where an examination area which exceeds the active height of the detector is involved. If the optically-defined examination area is smaller than the active surface or corresponds precisely to it, only the recording of a single radiographic image is necessary, this too being determined by the control device which then determines the corresponding optimum recording position.

The radiographic imaging in accordance with the invention thus allows an especially simple and largely automatic capture of the relevant data for recording the image. The doctor or the x-ray system operator merely has to optically mark the area for examination using the optical light marking device, whereby all the relevant information is automatically determined on the part of the control device and the corresponding image recording activities are activated. The relevant processing data, which comprises the maximum height of the individual image, where this height correlates with the maximum height of the active detector surface, is stored for this purpose by the control device. Further information is stored regarding the maximum number of images for a complete sequence, which can be predefined in relation to the maximum size of a relevant area under examination (e.g. of the spinal column). If necessary the corresponding parameter set can be selected as a function of a previous entry of the examination area.

Furthermore information relating to the overlapping area of two images to be linked to each other can be stored if the control device is embodied such that, when the height of a number of consecutive radiographic images to be recorded is determined, an overlapping area is to be taken into account. This overlapping area can be defined as a fixed area, measuring for example 3–5 cm, but it can also depend on the height of the final image determined.

In this case it is especially advantageous if the control device determines equal heights for all the individual radiographic images. This means that the control device "breaks down" the defined area of the patient into a number of subareas of equal size, each scanned with one radiographic image, which also has the advantage that the corresponding diaphragm setting for recording the relevant radiographic image does not have to be changed during the recording sequence, but rather that all the number of images can be taken at the same aperture.

In a further development of the inventive idea the width of the area of the patient to be recorded is also be able to be marked using the optical light marking device and the control device can be embodied for determining the width of the radiographic images to be recorded. Normal radiographic detectors have a width of 40 cm (as well as usually having a height of 40 cm) in which case the image width and thereby the radiographic slots may not exceed a maximum of 40 cm. Nevertheless a narrower radiographic slot can of course also be defined via the diaphragm, so that a narrower area of the patient is illuminated, which can be necessary depending on the type of examination. The control device is now embodied in accordance with the invention to determine the image width on the basis of the width of the optical marking, which, like the height, can also be set using the degree of opening of the diaphragm, e.g. on the basis of the setting parameters of the diaphragm and to make the corresponding settings at the diaphragm for image recording, so that fully automatic operation is implemented.

BRIEF DESCRIPTION OF THE DRAWINGS

Further advantages, features and details of the invention are produced by the exemplary embodiment described below, as well with reference to the drawings. The diagrams show.

DETAILED DESCRIPTION OF INVENTION

Figure 1:
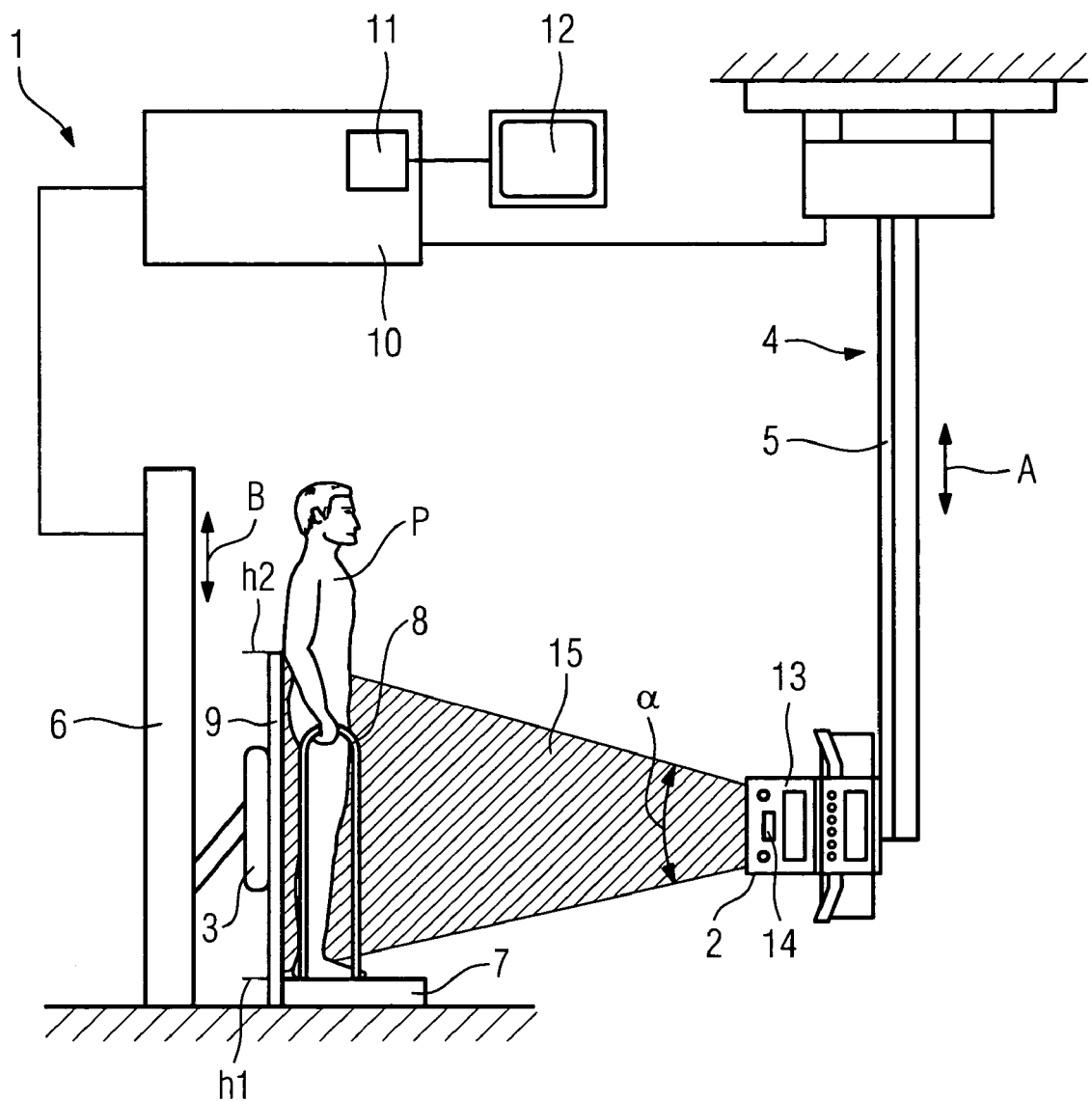
FIG. 1 a basic diagram of a radiographic imaging device in accordance with the invention, for the definition of the area of the patient, and FIG. 2 the radiographic imaging device from FIG. 1 during the execution of an image recording sequence.

FIG. 1 shows a radiographic imaging device 1 in accordance with the invention, consisting of a radiographic source 2, here an x-ray source, as well as a radiographic detector 3, here a digital solid-state detector. The radiographic source 2 is arranged on a stand 4 with a telescopic bar 5, which means that, as indicated by the double-headed arrow, it can be moved vertically. The same applies to the radiographic detector 3, which is also arranged on a stand 6, and, as indicated by the double-headed arrow B, can likewise be moved vertically. Whereas stand 4 is ceiling-mounted, stand 6 is a floor stand.

Near the radiographic detector a pedestal 7 of a predetermined height is provided, on which the patient P must stand for the image to be recorded. Arranged on either side of the pedestal 7 are supports 8 in the form of handrails which can be moved vertically, which the patient can hold onto since they must stand very still to enable the image to be recorded. Furthermore a rear radiation-transparent plate 9 is provided which is positioned to provide protection and prevents the patient touching the radiographic detector 3, which is arranged immediately behind plate 9.

The radiographic imaging device 1 in accordance with the invention further includes a central control device 10, featuring an integrated image processing device 11 as well as an assigned monitor 12. The control device 10 is used to shift the radiographic source 2 and the radiographic detector 3 in the vertical plane so that they can move to different imaging positions, in order to control image recording operation, which is also controlled via the control device 10. The image processing device integrated on the control side is used to calculate from the data relating to the individual images given to the control device an overall image which will subsequently be output on the monitor 12.

In the exemplary embodiment in accordance with FIG. 1 a diaphragm 13 is provided on the radiographic source 2 into which an optical light marking device 14, preferably a light sight, is integrated. Using this marking device it is possible to project onto the patient P an optical marking via the light cone 15 and from this to define the height of the area under examination to be recorded by individual radiographic images. This is done by moving the radiographic source into a corresponding position, after which the height and if necessary also the width of the light cone 15 determined via the marking device 14 are adjusted so that only the desired area of the patient is illuminated, with the setting preferably being undertaken so that the light cone 15 is symmetrical, to which end the height of the radiographic source must be adjusted if necessary.

The control device 10 is now in a position, using the height of the patient area defined via the optical marking device, to calculate the number and height of the images to be recorded necessary to produce a complete image of this area of the patient, which in the exemplary embodiment shown exceeds the height of the detector. This is possible, after on the one hand the geometrical circumstances, especially the distance of the radiographic source 2 or the marking device 14 as well as diaphragm 13 from the plane of the detector 3 is known to the control device, on the other hand the beam angle $\alpha$ (in the height) and if necessary a specifically set beam angle in the width of the radiation cone, defined by the setting of the diaphragm, is known to the control device 10, so that the precise height of the area under examination in the plane of the radiographic detector can actually be determined. In the example shown the area under examination runs from h1–h2, corresponding merely for reasons of providing an example here to the height of the transparent plate 9. This is however in no way mandatory, it can have other heights as well. The maximum height depends on how wide the diaphragm can be opened, meaning how large the angle $\alpha$ can be. With known diaphragms this is possible up to a maximum of around 180 cm in the plane of the radiographic detector. A width of maximum 40 cm is possible.

From the information at its disposal the control device 10 as described now calculates the height (and if necessary the width) of the area under investigation, in this case therefore the distance between h1 and h2. From this overall height the number and the height of the individual images will be calculated which are needed to produce an image of this overall height. In this case the individual parameters are calculated so that all radiographic images are the same height. For each radiographic image the relevant recording position of the radiographic source 2 and also of the radiographic detector 3 is then computed. Account is taken here of any image overlaps necessary in two adjacent images to enable them to be linked into the overall image. If all parameters are known the corresponding image recording setting parameters are calculated at the diaphragm, after which the image can be recorded.

Figure 2:
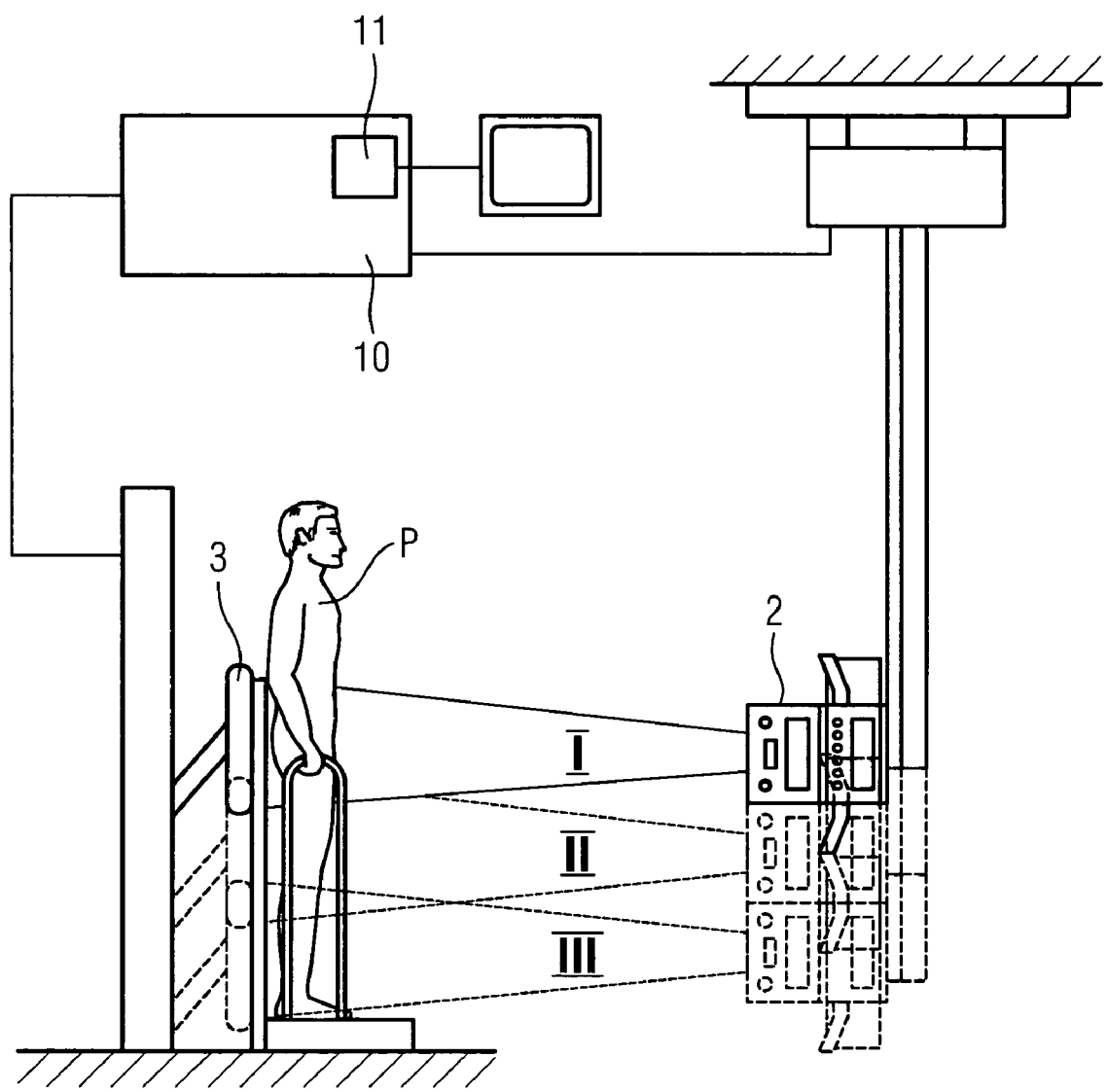

This sequence is shown in FIG. 2. In the example shown three separate recording positions are moved to, namely positions I, II and III, to which end the radiographic source 2 and the radiographic detector 3 are moved automatically via the control device 10. In each position a radiographic image is recorded. In the exemplary embodiment shown, three individual images are recorded to produce an image of the entire area of the patient, with the height of each image essentially utilizing the entire surface of the detector. It can be seen that the radiographic slots overlap in relevant recording positions, in order to record areas in two adjacent images which are identical and subsequently are used to link the two images.

Once all individual images are recorded, on the control device 10 or the image recording device 11 side the overall image which is subsequently output is determined.

As well as the recording of the height of the area of the patient to be scanned described, the control device 10 is also embodied to record the width of the area of the patient defined by the light cone 15, if this area is smaller than the active width of the radiographic detector 3. Using the diaphragm it is possible to influence the width of the light cone 15, it can be halved to 20 cm for example. The control device 10 is now in a position to determine the corresponding diaphragm setting parameters in relation to the width as well, which are then set for the individual images to be recorded, as shown in FIG. 2. That means that not only are the parameters for the height adjustment of the diaphragm determined, but also the diaphragm width if required.

The invention claimed is:

1. A medical imaging device, comprising:
   an X-radiation source;
   a digital radiation detector, the X-radiation source and the digital radiation detector movable relative to a patient in a standing position for positioning the X-radiation source and the digital radiation detector at imaging positions;
   a control device for controlling the moving of the X-radiation source and the digital radiation detector and for generating a viewable radiographic image; and
   an optical marking device arranged at the X-radiation source and configured to mark on the patient's body with visible illumination an elevation level of an examination area of the patient, wherein the control device is configured to determine a required quantity and height of individual radiographic images which show an entire examination area when the individual radiographic images are assembled into a combined image including the individual radiographic images, and to synchronously move the X-radiation source to a source imaging position, and the digital radiation detector to a detector imaging position, based on the elevation level of the examination area.

2. The medical imaging device according to claim 1, wherein the optical marking device is further configured to mark on the patient's body with visible illumination a width of the examination area and the control device is further configured to determined a required width of the individual radiographic images.

3. The medical imaging device according to claim 1, wherein the optical marking device includes a light source or a laser source.

4. The medical imaging device according to claim 3, wherein the optical marking device includes a visor.

5. The medical imaging device according to claim 1, wherein the optical marking device projects a measuring grid onto the patient for determining the elevation level of the examination area.

6. The medical imaging device according to claim 1, wherein the optical marking device projects a measuring grid onto the patient for determining the width of the examination area.

7. The medical imaging device according to claim 4, wherein the X-radiation source includes a diaphragm for adjusting an aperture of the X-radiation source and the optical marking device is included in the diaphragm.

8. The medical imaging device according to claim 1, wherein the individual radiographic images have the same height.

9. The medical imaging device according to claim 1, wherein the control device is further configured to determine an overlap area of the individual radiographic images so that the individual radiographic images overlap in the overlap area when assembled to the combined image.

10. The medical imaging device according claim 1, wherein the control system as further configured to successively move the X-radiation source and the digital image detector to a plurality of source image positions and detector image positions and to trigger an image recording at each source and detector image positions.

11. The medical imaging device according claim 1, wherein the X-radiation source includes a diaphragm for adjusting an aperture of the X-radiation source, the optical marking device is included in the diaphragm, and the control device is configured to automatically determine a required quantity and height of the individual radiographic images from a geometry of the distance of the radiographic source, the marking device, and the diaphragm from a plane of the detector to show the entire examination area when the individual radiographic images are assembled into the combined image including the individual radiographic images.

12. The medical imaging device according claim 1, wherein the X-radiation source includes a diaphragm for adjusting an aperture of the X-radiation source, the optical marking device is included in the diaphragm, and the control device is configured to automatically determine a required quantity, height, and width of the individual radiographic images from a geometry of the distance of the radiographic source, the marking device, and the diaphragm from a plane of the detector to show the entire examination area when the individual radiographic images are assembled into the combined image including the individual radiographic images.

* * * * *